United States Patent [19]

Pews

[11] 4,376,201

[45] Mar. 8, 1983

[54] PREPARATION OF 2-ALKYLPYRIMIDINES

[75] Inventor: Richard G. Pews, Midland, Mich.

[73] Assignee: The Dow Chemical Company, Midland, Mich.

[21] Appl. No.: 301,688

[22] Filed: Sep. 14, 1981

[51] Int. Cl.$^3$ .......................................... C07D 239/26
[52] U.S. Cl. .................................................. 544/242
[58] Field of Search ....................................... 544/242

[56] References Cited

U.S. PATENT DOCUMENTS 3,050,523  8/1962  Erner et al. ........................... 544/242
3,366,634  1/1968  McBride, Jr. et al. .............. 544/242

FOREIGN PATENT DOCUMENTS 2701372  7/1978  Fed. Rep. of Germany ...... 544/242

OTHER PUBLICATIONS

"The Pyrimidines", Interscience Publishers (1962), pp. 455, 445-448.
Okada, et al., Chemical Abstracts, vol. 85, 142251m (1976).
Tsuchiya, et al., Chemical Abstracts, vol. 86, 29475h (1977).
Disteldorf, et al., Chemical Abstracts, vol. 89, 180044m (1978).
Lythgoe, et al., J. Chem. Soc., 1951, pp. 2323-2329 (1951).

*Primary Examiner*—Donald G. Daus
*Assistant Examiner*—Diana G. Rivers

[57] ABSTRACT

A 3-aminopropyl carboxylic acid amide is dehydrogenated and cyclized over a supported platinum or palladium catalyst to prepare 2-alkylpyrimidines in a single step vapor phase reaction.

5 Claims, No Drawings

PREPARATION OF 2-ALKYLPYRIMIDINES

BACKGROUND OF THE INVENTION

The preparation of pyrimidines and 2-alkylpyrimidines by the reaction of an alkylene 1,3-diamine with an organic carboxylic acid, ester or amide over a supported noble metal catalyst is taught in U.S. Pat. No. 3,050,523. This reference teaches the cyclization of, for example, an organic carboxylic acid amide followed by dehydrogenation. The steps of the work-up and separation of product by the method taught in this reference are time consuming and cumbersome and the resulting yields are not commercially attractive.

SUMMARY OF THE INVENTION

I have now found that 2-alkylpyrimidines may be prepared in good yields and purity by a single step vapor phase reaction wherein a 3-aminopropyl carboxylic acid amide is dehydrogenated and cyclized over a supported platinum or palladium catalyst.

DETAILED DESCRIPTION OF THE INVENTION

The reaction may be carried out neat, i.e., in the absence of a solvent, but is optionally carried out in a solvent such as, for example, pyridine. In accordance with the invention, a solution of the desired aminoamide is advantageously fed through a heated reactor containing the supported catalyst. At the completion of the reaction, the solvent, if present, is then removed by distillation and further distillation of the pot residue provides the desired product.

The reactor is advantageously heated to a temperature of from 250° to 400° C., preferably 330° to 350° C. The catalyst advantageously comprises from 0.1 to 5 percent by weight of platinum or palladium supported on silica gel, carbon, magnesia or, preferably, alumina. The preferred catalyst comprises about 0.5 percent by weight palladium or platinum on α-alumina. Feed rates to the reactor were 20 to 150 ml/hr, preferably 40 to 80 ml/hr.

The invention is further illustrated by the following example.

EXAMPLE 1

A pyridine solution of 3-aminopropylpivalamide (approximately 35 percent by weight aminoamide) was fed continuously to a heated 1"×20" reactor maintained at 330° to 345° C. The reactor was packed with 50 g of 0.5 percent palladium on alumina. After removal of pyridine by distillation, the product, 2-t-butylpyrimidine was obtained, b.p. 160° to 163° C.

Various modifications may be made in the present invention without departing from the spirit or scope thereof and it is understood that I limit myself only as defined in the appended claims.

I claim:

1. A process for making 2-alkylpyrimidines which comprises dehydrogenating and cyclizing a 3-aminopropyl carboxylic acid amide in a single step vapor phase reaction over a supported platinum or palladium catalyst.

2. Process of claim 1 wherein the carboxylic acid amide is 3-aminopropylpivalamide.

3. Process of claim 2 wherein the catalyst is 0.5 percent palladium on alumina.

4. Process of claim 2 wherein the catalyst is 0.5 percent platinum on alumina.

5. Process of claim 3 wherein the reaction is carried out at 330° to 345° C.

* * * * *